United States Patent
Xie

(10) Patent No.: US 10,132,847 B2
(45) Date of Patent: Nov. 20, 2018

(54) TOMOGRAPHY OF MULTIPHASE MIXTURES

(71) Applicant: SCHLUMBERGER TECHNOLOGY CORPORATION, Sugar Land, TX (US)

(72) Inventor: Cheng-Gang Xie, Sawston (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 634 days.

(21) Appl. No.: 13/691,435

(22) Filed: Nov. 30, 2012

(65) Prior Publication Data

US 2013/0144548 A1     Jun. 6, 2013

Related U.S. Application Data

(60) Provisional application No. 61/567,266, filed on Dec. 6, 2011.

(51) Int. Cl.
*G01R 27/00*     (2006.01)
*G06F 15/00*    (2006.01)
(Continued)

(52) U.S. Cl.
CPC .............. *G01R 27/00* (2013.01); *G01F 1/56* (2013.01); *G01F 1/60* (2013.01); *G01F 1/74* (2013.01);
(Continued)

(58) Field of Classification Search
CPC ....................................................... G01F 1/74
(Continued)

(56) References Cited

U.S. PATENT DOCUMENTS 5,485,743 A     1/1996   Taherian et al.
6,655,221 B1   12/2003  Aspelund et al.
(Continued)

FOREIGN PATENT DOCUMENTS

WO    2008046805         4/2008
WO    2009030870 A1     3/2009

OTHER PUBLICATIONS

Cornelliussen et al., "Handbook of Multiphase Flow Metering," Norwegian Society for Oil and Gas Measurement, Mar. 2005: pp. 1-113.
(Continued)

*Primary Examiner* — Manuel L Barbee
*Assistant Examiner* — Raymond Nimox

(57) ABSTRACT

A tomography system for determining properties of flowing multiphase fluid, comprising a duct having a duct wall and interior space within the duct wall for carrying a flow of the multiphase fluid and a plurality of sensors, which are electrodes or coils, at positions distributed around the duct wall on a planar cross section through the duct, wherein the sensors (electrodes or coils) are used for making a plurality of measurements of electrical or magnetic properties through the duct wall and the multiphase fluid; and a processor is used to receive measurement data from the sensors and to compute from the measured properties to derive quantitative values of at least one property selected from permittivity, conductivity, magnetic permeability and complex-conductivity of the multiphase fluid independent of effects external to the fluid flow, such as effects of the duct walls and the geometry of the positioning of the sensors (electrodes or coils).

20 Claims, 13 Drawing Sheets

(51) Int. Cl.
      *G01F 1/56* (2006.01)
      *G01F 1/60* (2006.01)
      *G01F 1/74* (2006.01)
      *G01N 27/02* (2006.01)
      *G01N 33/28* (2006.01)

(52) U.S. Cl.
      CPC ....... *G01N 27/023* (2013.01); *G01N 33/2823* (2013.01); *G06F 15/00* (2013.01)

(58) Field of Classification Search
      USPC .......................................................... 702/65
      See application file for complete search history.

(56) References Cited

U.S. PATENT DOCUMENTS

| | | | |
|---|---|---|---|
| 6,831,470 | B2 | 12/2004 | Xie et al. |
| 7,908,930 | B2 | 3/2011 | Xie et al. |
| 8,027,794 | B2 | 9/2011 | Xie |
| 8,536,883 | B2 | 9/2013 | Xie et al. |
| 2001/0050881 | A1 | 12/2001 | DePaoli et al. |
| 2003/0011386 | A1* | 1/2003 | Xie et al. ............... 324/694 |
| 2007/0124091 | A1* | 5/2007 | Wee .......................... 702/49 |
| 2007/0279073 | A1* | 12/2007 | Wee .......................... 324/639 |
| 2008/0319685 | A1* | 12/2008 | Xie et al. ................. 702/45 |
| 2009/0088985 | A1* | 4/2009 | Wee .......................... 702/30 |
| 2009/0126502 | A1* | 5/2009 | Wee et al. ............... 73/861.04 |
| 2009/0204346 | A1* | 8/2009 | Xie ........................... 702/45 |
| 2010/0213953 | A1 | 8/2010 | Yang et al. |
| 2011/0267074 | A1 | 11/2011 | Xie et al. |
| 2011/0290035 | A1* | 12/2011 | Wee et al. ............... 73/861.04 |

OTHER PUBLICATIONS

Cui et al., "Image reconstruction for field-focusing capacitance imaging," Meas. Sci. Technol., 2011, vol. 22: pp. 1-9.

Kjaersgaard-Rasmussen et al., "Inside-out electrical capacitance tomography," Flow Measurement and Instrumentation, 2011, vol. 22: pp. 104-109.

Leeungculsatien et al., "Continuous Phase Velocity Profile Measurement in Multiphase Flow Using a Non-invasive Multi-Electrode Electromagnetic Flow Meter," AIP Conf. Proc., The 7th International Symposium on Measurement TEchniques for Multiphase Flows, Sep. 2011, vol. 1428: pp. 1-8.

Li et al., "Image reconstruction by nonlinear Landweber iteration for complicated distributions," Meas. Sci. Technol., 2008, vol. 19: pp. 1-8.

Qui et al., "Engineering and application of a dual-modality process tomography system," Flow Measurement and Instrumentation, 2007, vol. 18: pp. 247-254.

Xie, "Measurement of Multiphase Flow Water Fraction and Watercut," Multiphase Flow: The Ultimate Measurement Challenge, Proceedings of the 5th International Symposium on Measurement Techniques for Multiphase Flows, Dec. 2006, vol. 914: pp. 232-239.

Xie et al., "Electrical capacitance tomography for flow imaging: system model for development of image reconstruction algorithms and design of primary sensors," IEE Proceedings-G, Feb. 1992, vol. 139(1): pp. 89-98.

Xie et al., "Multiphase Flow Measurement in Oil and Gas Production," 5th World Congress on Industrial Process Tomography, 2007: pp. 1-12.

Yang, "Calibration of capacitance tomography systems: a new method for setting system measurement range," Meas. Sci. TEchnol., 1996, vol. 7: pp. 863-867.

Yang et al., "Development of capacitance tomographic imaging systems for oil pipeline measurements," Rev. Sci. Instrum. Aug. 1995, vol. 66(8): pp. 4326-4332.

Yang, "An Improved Normalisation Approach for Electrical Capacitance Tomography," 1st World Congress on Industrial Process Tomography, Apr. 1999: pp. 215-218.

International Search Report of PCT Application No. PCT/IB2012/057024 dated May 15, 2013: pp. 1-4.

Anonymous, "The Roxar Multiphase meter 2600 Based on Zector technology," Emerson Process Management Brochure, Feb. 2009, Brochure retrieved Jun. 5, 2014: pp. 1-7.

\* cited by examiner

TOMOGRAPHY OF MULTIPHASE MIXTURES

CROSS-REFERENCE TO RELATED APPLICATION

This application claims the benefit of U.S. Provisional Patent Application 61/567266 filed Dec. 6, 2011, which is incorporated herein by reference in its entirety.

BACKGROUND

Performing tomography on multiphase mixtures is a way to determine properties of the multiphase mixture, where the properties may be measured in a pipeline, conduit, wellbore or other structure carrying flow of a multiphase mixture.

The challenge with multiphase flow measurement is that both the phase distribution and the phase velocity profile vary significantly in time and space, as manifested by various flow regimes (patterns) mapped for different pipe deviations, typically as a function of liquid-liquid or gas-liquid superficial velocities. Process tomography has been conceived to have the potential of measuring dynamic multiphase processes such as multiphase flows of complex regimes through a pipeline or in a process vessel. The basic concept is to mathematically reconstruct, from appropriate multiple measurements made at a pipe/vessel periphery, the phase holdup and/or phase velocity profiles, at a sufficient spatial and temporal resolution.

The term "holdup" denotes the fraction of a particular fluid present in a cross-section of pipe. Because each fluid moves at a different speed due to different gravitational forces and other factors, the holdup of a particular fluid is not the same as the volumetric-flow-rate proportion of the total volumetric flow rate due to that fluid. Individual volumetric flow rate can be derived by integrating phase holdup and phase velocity profiles over the pipe cross-section.

A lot of academic and industrial research efforts have been devoted to imaging multiphase flow phase holdup, based on electrical capacitance tomography (ECT), electrical resistance tomography (ERT), electrical impedance tomography (EIT), electrical magnetic tomography (EMT), and their combinations such as ECT and ERT. Research effort has also been put into other ways of measuring multiphase flow. For some of the electrical tomography sensing techniques, processing of the experimental data has been problematic. For instance US patent application 2010/0213953A1 (relating to a method and apparatus for producing particle density map images of particles in a fluidized bed apparatus by ECT) describes a capacitance measurement normalization model which does not permit the auto-removal of effects of pipe-wall capacitance(s), and furthermore, the images reconstructed on the basis of such normalized capacitances only provide an indirect, qualitative result of flow mixture dielectric constant or permittivity.

SUMMARY

This summary is provided to introduce a selection of concepts that are further described below. This summary is not intended to be used as an aid in limiting the scope of the subject matter claimed.

Broadly, the present disclosure provides a tomography system for measurement of multiphase flow in which a processor such as a computer is configured to compute quantitative values of permittivity, conductivity, magnetic permeability and/or complex-permittivity/-conductivity of the multiphase fluid from the measured properties representative of capacitance, conductance (which may be measured as its reciprocal which is resistance), inductance and/or admittance (which may be measured as its reciprocal which is impedance). Electrical or magnetic tomography as disclosed here can provide robust determination of properties of the flow, such as mixture permittivity or conductivity.

In one aspect, there is disclosed an electrical or magnetic tomography system for determining properties of flowing multiphase fluid, comprising:

a duct for carrying a flow of a multiphase fluid;

a plurality of sensors which are electrodes and/or coils at positions distributed around the duct on a planar cross section through the duct, for measuring properties of the multiphase fluid; and a processor receiving measurement data from the sensors and configured to determine quantitative values of permittivity, conductivity, magnetic permeability and/or complex-permittivity/conductivity of the multiphase fluid from the measured properties representative of capacitance, conductance, inductance and/or admittance.

The processor may be configured to determine a distribution of one or more of the quantitative values permittivity, conductivity, magnetic permeability and/or complex-permittivity/conductivity within the cross-section.

It is possible that the system will have groups of sensors, with the sensors in one group distributed around one cross section through the duct and the sensors in other groups distributed around respective different cross-sections through the duct. In such a case, the sensors in each group may be used to make in-plane measurements but it is also possible that sensors in different groups could be used to make cross-plane measurements.

The duct may be circular in cross-section, but it is also possible that it will have some other cross-section such as square or rectangular.

In a second aspect there is provided a computer implemented method of measuring properties of flowing multiphase fluid, comprising making a plurality of measurements representative of capacitance, conductance, inductance, or admittance at one or more cross sections through the duct and computing permittivity, conductivity, magnetic permeability and/or complex-permittivity/conductivity of the multiphase fluid from the measurements made.

In embodiments of this disclosure, the values of permittivity, conductivity, magnetic permeability and/or complex-permittivity/conductivity may be used to compute phase holdups (or fractions) such as the gas fraction, the water fraction and the water-in-liquid ratio (WLR) of a multiphase flow. This may for example, be an oil-continuous flow, a water-continuous flow, or a gas-continuous flow, or a flow which is a combination of oil-continuous, water-continuous and/or gas-continuous flow. They may also be used to compute, using a direct and/or iterative algorithm, a quantitative reconstruction of the distribution of permittivity, conductivity, magnetic permeability and/or complex-permittivity/-conductivity of the multiphase flow, in two-dimensional (2D) and/or three-dimensional (3D) space, and/or in time. Such a computed reconstruction may be displayed or otherwise output as a graphic 2D and/or 3D image(s).

The electrical or magnetic tomographic methods disclosed here may be used together with other measuring methods, such as a Venturi, a gamma-ray or X-ray densitometer, and in combination with a multi-energy gamma-ray or multi-energy X-ray system.

DETAILED DESCRIPTION

Figure 1:
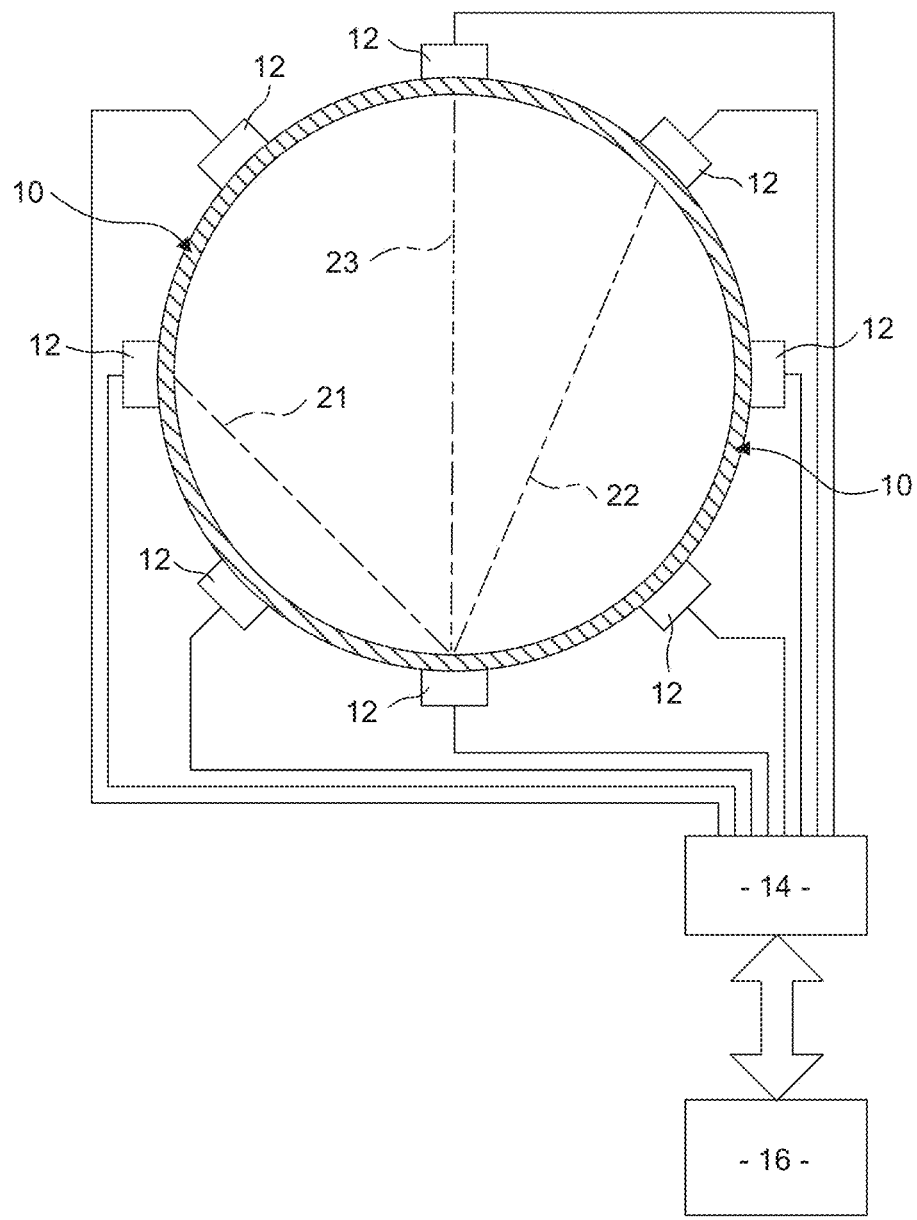
FIG. 1 shows a cross section of a pipe for a multiphase flow.

FIG. 1 shows a portion of pipe 10 used to carry a multiphase flow. It is seen as an illustration here in one cross section transverse to the pipe axis and it is surrounded by a plurality of sensors, which here are electrodes 12, positioned in the plane of the cross section. These electrodes make measurements in a non-contact manner because they are at the exterior of a portion of pipe 10. This portion of pipe 10 is made from an electrically insulating and non-magnetic material, possibly a ceramic. The electrodes 12 make measurements through the pipe wall and the multiphase flow within the pipe. However, it is also possible to make measurements in a contact manner, with the electrodes being embedded in the insulating material so as to lie flush with its interior surface and in contact with the multiphase flow. The electrodes 12 are connected to an electronics package 14 for multiplexing among the electrodes to make measurements and the electronics package is in turn connected to a processor such as a computer 16 for controlling excitation of the electrodes, data collection and processing of the data obtained.

The electrodes are operated to measure a property which may be capacitance, resistance (or its reciprocal which is conductance), inductance or impedance (or its reciprocal admittance) between individual pairs of electrodes. If the total number of electrodes is N, a total of N(N-1)/2 independent measurements may be obtained by making measurements between each electrode and every other electrode.

In some embodiments of the present disclosure which will now be explained further by way of example, the electrodes measure capacitance between electrode pairs and so provide an ECT system for tomographic capacitance measurements of multiphase flow in the pipe. The capacitance of the fluid in the pipe is in series with the capacitance of the pipe wall and, as has been disclosed in the literature, the measurements obtained using the electrodes 12 can be processed to obtain multi-view (normalised) capacitance values which do not include the pipe wall capacitance.

As a preliminary, two calibration measurements are made. Low-calibration raw capacitance measurements $C_l$ (containing N(N-1)/2 independent electrode-pair measurements for an N-electrode system) are made using a material with known low-permittivity ($\varepsilon_l$) (such as empty-pipe air or dry gas), followed by high-calibration capacitance measurements $C_h$ using a material of known high-permittivity ($\varepsilon_h$) (such as full-pipe oil or an oil-water uniform mixture with a known WLR).

A parallel-capacitance normalization model has been used in prior publications to derive the (measured) normalized capacitances $C_n$ from the raw capacitances $C_m$ $$C_{n,parallel} = \frac{C_m - C_l}{C_h - C_l} \quad (1)$$

The effective capacitance of the electrically insulating pipe wall ($C_{wall}$), seen by each pair of the selected electrodes, is considered to be in series with the (unknown) fluid capacitance $C_x$. A ceramic material may be used for the insulating pipe wall to provide a stable value of $C_{wall}$. The measured raw capacitances of the unknown fluid ($C_m$), of the low-permittivity calibration material ($C_l$) and of the high-permittivity calibration material ($C_h$) are then as follows:

$$\frac{1}{C_m} = \frac{1}{C_{wall}} + \frac{1}{C_x(\varepsilon_m)}; \quad (2a)$$

$$\frac{1}{C_l} = \frac{1}{C_{wall}} + \frac{1}{C_x(\varepsilon_l)}; \quad (2b)$$

$$\frac{1}{C_h} = \frac{1}{C_{wall}} + \frac{1}{C_x(\varepsilon_h)}; \quad (2c)$$

Substituting Equations (2a) to (2c) into Equation (1) provides:

$$C_{n,parallel} = \frac{\left(\frac{1}{C_{wall}} + \frac{1}{C_x(\varepsilon_m)}\right)^{-1} - \left(\frac{1}{C_{wall}} + \frac{1}{C_x(\varepsilon_l)}\right)^{-1}}{\left(\frac{1}{C_{wall}} + \frac{1}{C_x(\varepsilon_h)}\right)^{-1} - \left(\frac{1}{C_{wall}} + \frac{1}{C_x(\varepsilon_l)}\right)^{-1}} \quad (3)$$

The (unknown) fluid only capacitance $C_x$ can be assumed to be proportional to the dielectric constant $\varepsilon_m$ of the bulk fluid as follows (where k are proportional/geometrical constants for the different electrode pairs), viz.

$$C_x(\varepsilon_m) = k\varepsilon_m \quad (4a)$$

$$C_x(\varepsilon_l) = k\varepsilon_l \quad (4b)$$

$$C_x(\varepsilon_h) = k\varepsilon_h \quad (4c)$$

And then Equation (3) can be written as:

$$C_{n,parallel} = \frac{\left(\frac{1}{C_{wall}} + \frac{1}{k\varepsilon_m}\right)^{-1} - \left(\frac{1}{C_{wall}} + \frac{1}{k\varepsilon_l}\right)^{-1}}{\left(\frac{1}{C_{wall}} + \frac{1}{k\varepsilon_h}\right)^{-1} - \left(\frac{1}{C_{wall}} + \frac{1}{k\varepsilon_l}\right)^{-1}} \quad (5)$$

Figure 2:
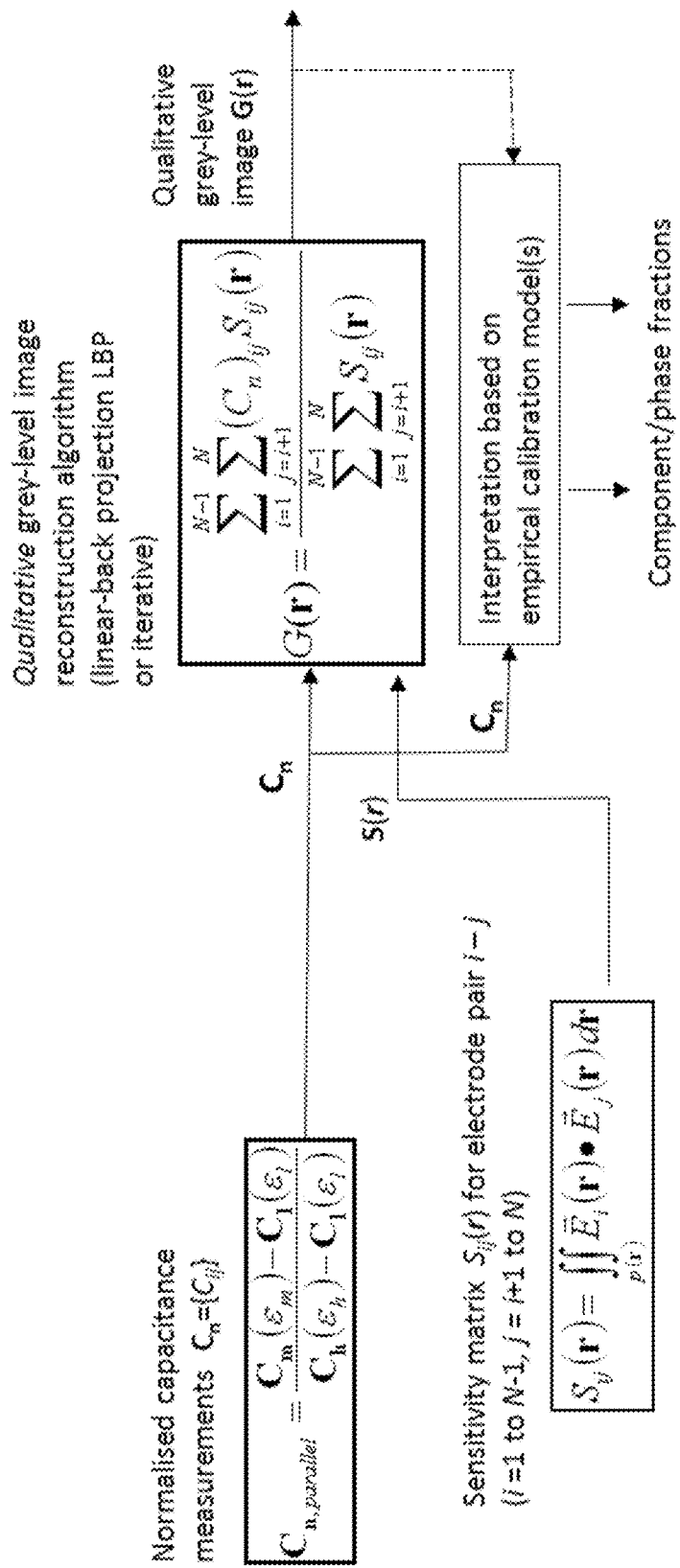
FIGS. 2 and 3 diagrammatically illustrate prior art calculation procedure for qualitative image reconstruction from ECT measurements.

Prior publications have disclosed a qualitative image reconstruction method based on the normalized capacitance $C_{n,parallel}$. This is illustrated in FIG. 2, with the linear back-projection (LBP) algorithmic equations (as shown in the figure) as an example. Phase fraction determination in this method is largely based on an empirical model which assumes that $C_{m,parallel}$ is proportional to $\varepsilon_m$. (This is only true if $C_{wall} \gg k\varepsilon_m$).

A series-capacitance normalization model has previously been proposed to derive alternative (measured) normalized capacitances $C_n$ from the raw capacitances $C_m$, viz.

$$C_n = \frac{\frac{1}{C_m} - \frac{1}{C_l}}{\frac{1}{C_h} - \frac{1}{C_l}} \quad (6)$$

From Equations (2a) to (2c), and Equations (4a) to (4c), the (measured) normalized capacitances $C_n$ can be related to the ultimately desired (fluid-only) mixture permittivity $\varepsilon_m$, as follows:

$$C_n = \frac{\left(\frac{1}{C_{wall}} + \frac{1}{C_x(\varepsilon_m)}\right) - \left(\frac{1}{C_{wall}} + \frac{1}{C_x(\varepsilon_l)}\right)}{\left(\frac{1}{C_{wall}} + \frac{1}{C_x(\varepsilon_h)}\right) - \left(\frac{1}{C_{wall}} + \frac{1}{C_x(\varepsilon_l)}\right)} \quad (7)$$

$$= \frac{\frac{1}{C_x(\varepsilon_m)} - \frac{1}{C_x(\varepsilon_l)}}{\frac{1}{C_x(\varepsilon_h)} - \frac{1}{C_x(\varepsilon_l)}}$$

$$= \frac{\frac{1}{\varepsilon_m} - \frac{1}{\varepsilon_l}}{\frac{1}{\varepsilon_h} - \frac{1}{\varepsilon_l}}$$

Using this approach, the wall-capacitances $C_{wall}$ (and the sensors' geometrical factors k) are substantially removed in the normalized (measured) capacitances $C_n$, by the use of the series-capacitance model of Equation (6). However, it can be seen from Equation (7) that, the resulting normalized capacitances $C_n$ are a nonlinear function of the desired mixture permittivity $\varepsilon_m$, which is to be measured and/or to be imaged.

Figure 3:
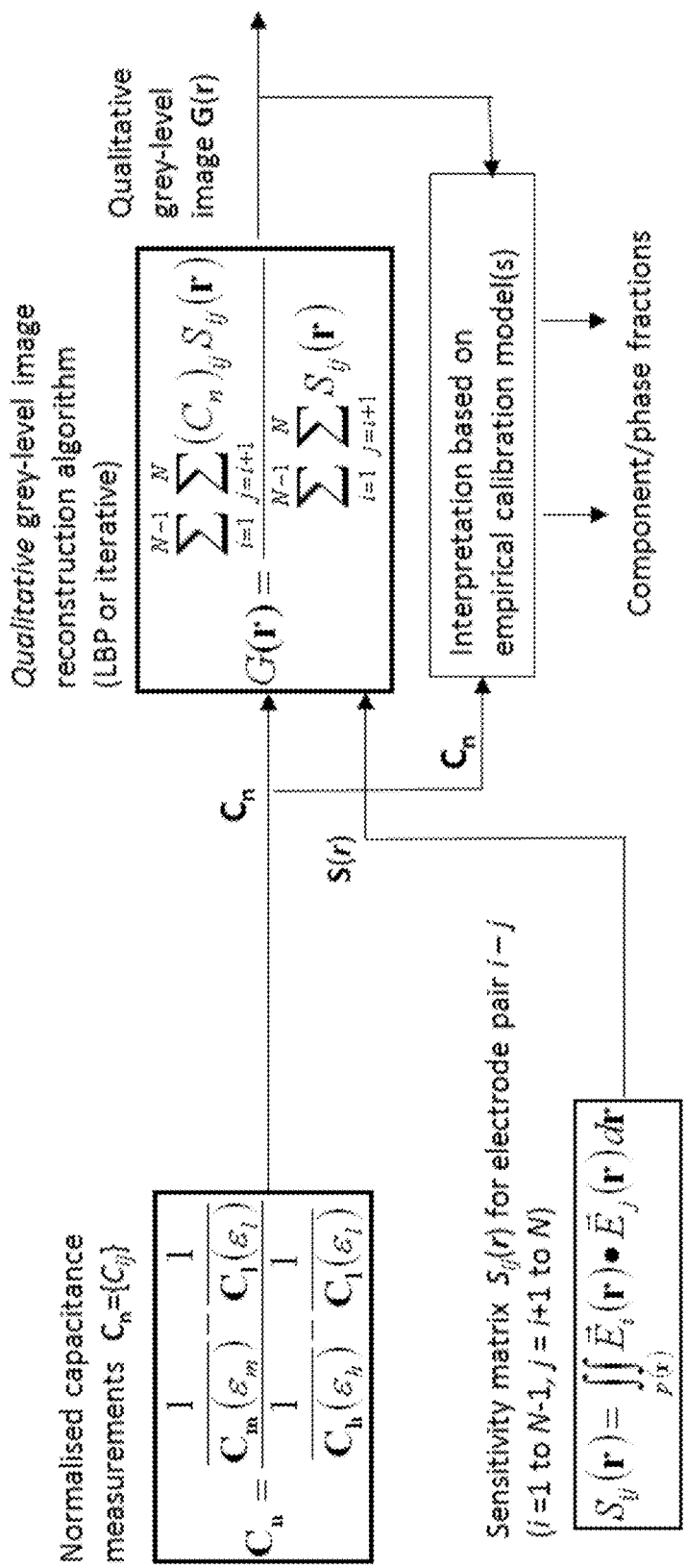

A qualitative image reconstruction method based on the series-model normalized capacitance $C_n$ has been proposed in prior documents and is illustrated in FIG. 3, with the linear back-projection (LBP) algorithm as an example. Phase fraction determination in this method is largely based on $C_n$ and an empirical (calibration) model.

In embodiments of the present disclosure, and in contrast with prior disclosures, measured multi-view (normalized) capacitances $C_n$ (that are free from the effects of pipe-wall capacitances and the sensors' geometrical factors k) are converted to a fundamental physics parameter—the corresponding multi-view mixture permittivity $\varepsilon_m$. These multi-view mixture permittivities $\varepsilon_m$ (which depend only on what is present in the flow in the pipe 10) may then be used as input to an image reconstruction step, removing the issues of the nonlinearity in the imaging domain and of the empirical correlations/calibrations in the subsequent step(s) of determining phase fractions based on $C_n$. This may then be used to compute the WLR, water fraction and/or gas-fraction, with the use of an appropriate dielectric mixing model(s). Based on the multi-view permittivity $\varepsilon_m$ data, a direct and/or iterative quantitative reconstruction of the mixture-permittivity distribution can be made.

Rearranging Equation (7) provides:

$$\varepsilon_m = \frac{1}{C_n\left(\frac{1}{\varepsilon_h} - \frac{1}{\varepsilon_l}\right) + \frac{1}{\varepsilon_l}} \quad (8)$$

Figure 4:
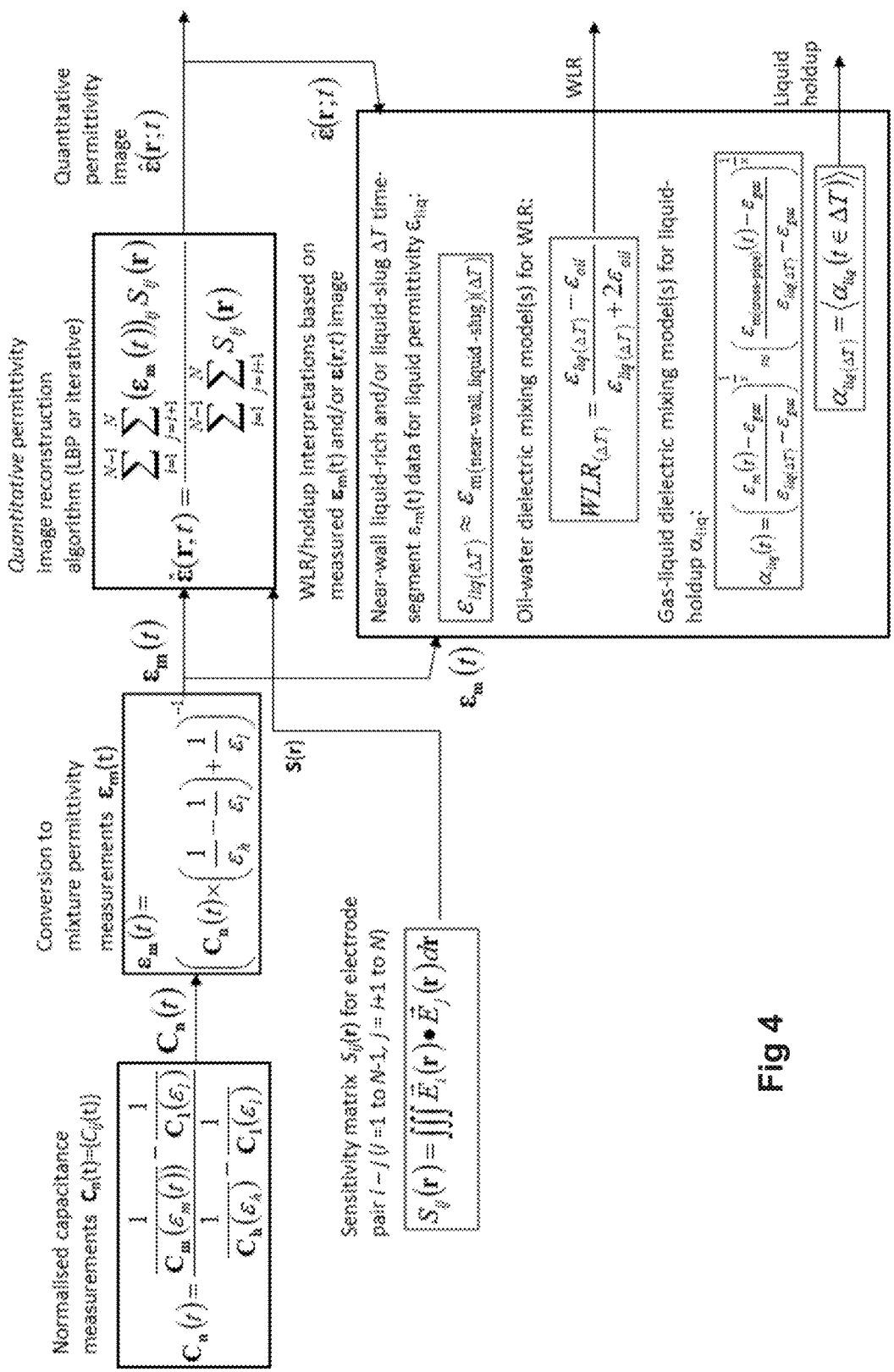
FIGS. 4 and 5 diagramatically illustrate calculation procedure for quantitative image reconstruction from ECT measurements.

Quantitative image reconstruction (at time instant t), based on this conversion to permittivity more accurately processes capacitance measurements into an image directly representing the permittivity properties of a multiphase mixture. An embodiment is shown by FIG. 4. A linear back-projection (LBP) algorithm is modified from that shown in FIG. 3 to use the measured $\varepsilon_m(t)$ as the input and provides the reconstructed image of the mixture-permittivity space-time distribution $\varepsilon_m(r;t)$ as output (r=(x,y,z)). Iterative image reconstruction algorithms using the measured $\varepsilon_m(t)$ as the input may be used in addition to or in place of the LBP algorithm; processing in this way overcomes distribution-dependent 'softfield' effects.

The output of the reconstruction of mixture-permittivity distribution $\varepsilon_m(r;t)$, which may be processed to indicate the underlying flow-regime information, may be used as input to the WLR and/or liquid-fraction/holdup interpretation, as illustrated in FIG. 4.

Figure 5:
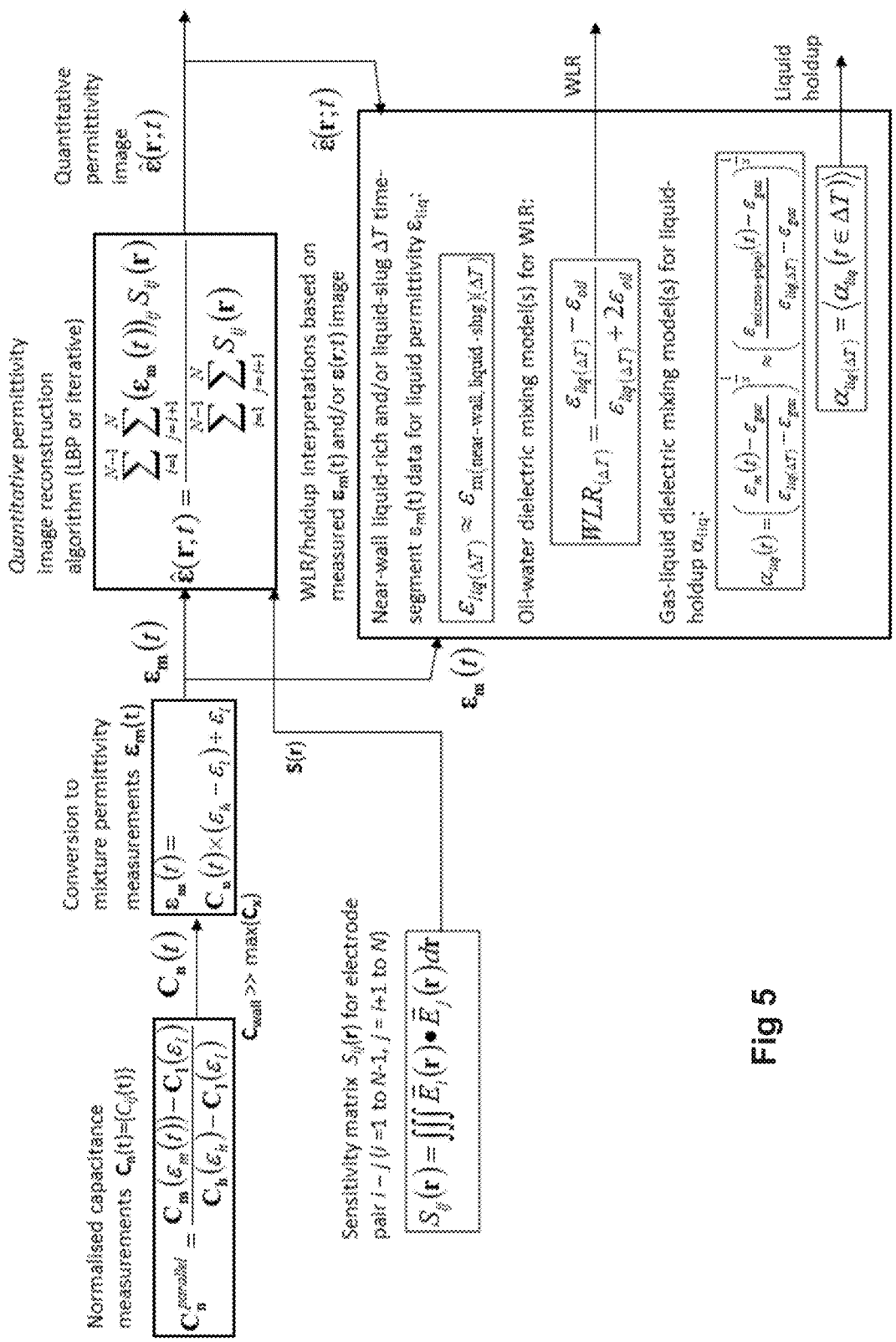

Another embodiment of the present disclosure uses the parallel-capacitance normalization model above. The sensing electrodes 12 are designed with a very thin dielectric coating on the electrodes such that the pipe-wall capacitance is much larger than the expected maximum of the fluid capacitance, which can be expressed as $C_{wall} \gg \max(C_x)$. Then $C_m \cong C_x$ and Equation (5) reduces to $C_{n,parallel} \cong (\varepsilon_m - \varepsilon_l)/(\varepsilon_h - \varepsilon_l)$ so that $C_{n,parallel}$ is proportional to $\varepsilon_m$. This provides a way to convert to permittivity measurements and, as shown by FIG. 5, the measured $\varepsilon_m$, where $\varepsilon_m = C_{n,parallel}(\varepsilon_h - \varepsilon_l) + \varepsilon_l$, can be used as input to an LBP algorithm and/or iterative image reconstruction algorithms so as to obtain the reconstructed image of the mixture-permittivity distribution $\varepsilon_m(r)$, and the multiphase-flow WLR and liquid holdup as outputs.

In some other embodiments of the present disclosure, the electrodes 12 shown in FIG. 1 measure resistance or conductance between electrode pairs and so provide an ERT system for tomographic resistance measurements of multiphase flow in pipe 10. (Resistance is of course the reciprocal of conductance).

The measured multi-view (normalised) conductances $G_n$ (that are free from the effects of electrode contact conductances) are converted to multi-view mixture conductivities $\sigma_m$. These flow-dependent-only conductivities $\sigma_m$ may then be converted to the WLR and/or liquid-fraction, with the use of conductivity mixing model(s). Based on the multi-view $\sigma_m$ data, a direct and/or iterative quantitative reconstruction of the mixture-conductivity distribution may be made. The mathematical treatment is analogous to that given above for capacitance, as will now be shown.

To perform an appropriate calibration of the ERT system, low-calibration raw conductance measurements $G_l$ may be made by using a material with known low-conductivity ($\sigma^l$) (such as full-pipe fresh water), followed by high-calibration ones $G_h$ by using a material of a known high-conductivity ($\sigma_h$) (such as full-pipe salty water).

The effective contact resistance ($R_{contact}$) of the electrodes of an ERT sensor is in series with the fluid (unknown) resistance $R_x$ (the electrode material may be chosen so that $R_{contact}$ is small and/or is stable).

The measured raw conductances of the unknown fluid ($G_m$), of the low-conductivity calibration material ($G_l$) and of the high-conductivity calibration material ($G_h$) are then as follows (from $R_m = R_{contact} + R_x$):

$$\frac{1}{G_m} = \frac{1}{G_{contact}} + \frac{1}{G_x(\sigma_m)}; \quad (102a)$$

-continued $$\frac{1}{G_l} = \frac{1}{G_{contact}} + \frac{1}{G_x(\sigma_l)}; \quad (102b)$$

$$\frac{1}{G_h} = \frac{1}{G_{contact}} + \frac{1}{G_x(\sigma_h)}; \quad (102c)$$

The fluid only (unknown) conductance $G_x$ can be assumed to be proportional to the conductivity $\sigma_m$ of the bulk fluid as follows (where k are proportional/geometrical constants for the different electrode pairs), viz.

$$G_x(\sigma_m) = k\sigma_m \quad (104a)$$

$$G_x(\sigma_l) = k\sigma_l \quad (104b)$$

$$G_x(\sigma_h) = k\sigma_h \quad (104c)$$

A normalisation model (analogous to the series-capacitance model at Equation (6) above) can be used to derive the measured) normalised conductances $G_n$ from the raw conductances $G_m$, viz.

$$G_n = \frac{\frac{1}{G_m} - \frac{1}{G_l}}{\frac{1}{G_h} - \frac{1}{G_l}} \quad (106)$$

From Equations (102a) to (102c), and Equations (104a) to (104c), it is then possible to relate the (measured) normalised conductances $G_n$ to the ultimately desired (fluid-only) mixture conductivity $\sigma_m$, as follows:

$$G_n = \frac{\left(\frac{1}{G_{contact}} + \frac{1}{G_x(\sigma_m)}\right) - \left(\frac{1}{G_{contact}} + \frac{1}{G_x(\sigma_l)}\right)}{\left(\frac{1}{G_{contact}} + \frac{1}{G_x(\sigma_h)}\right) - \left(\frac{1}{G_{contact}} + \frac{1}{G_x(\sigma_l)}\right)}$$

$$= \frac{\frac{1}{G_x(\sigma_m)} - \frac{1}{G_x(\sigma_l)}}{\frac{1}{G_x(\sigma_h)} - \frac{1}{G_x(\sigma_l)}}$$

$$= \frac{\frac{1}{\sigma_m} - \frac{1}{\sigma_l}}{\frac{1}{\sigma_h} - \frac{1}{\sigma_l}} \quad (107)$$

In this way, the electrode contact conductances $G_{contact} = 1/R_{contact}$ and also the sensors' geometrical factors k are substantially removed. However, it can be seen from Equation (107) that the resulting normalized conductances $G_n$ are a nonlinear function of the desired mixture conductivity $\sigma_m$ to be measured and/or to be imaged.

In embodiments of the present disclosure, the normalised conductances $G_n$ are converted to the mixture conductivity $\sigma_m$ which is a fundamental physics parameter and this mixture-conductivity ($\sigma_m$) is itself used as the input to the image reconstruction step, removing the issues of the non-linearity in the imaging domain and of the empirical correlations/calibrations in the subsequent step(s) of determining phase fractions based on $G_n$.

Rearranging Equation (107) gives $$\sigma_m = \frac{1}{G_n\left(\frac{1}{\sigma_h} - \frac{1}{\sigma_l}\right) + \frac{1}{\sigma_l}} \quad (108)$$

Figure 6:
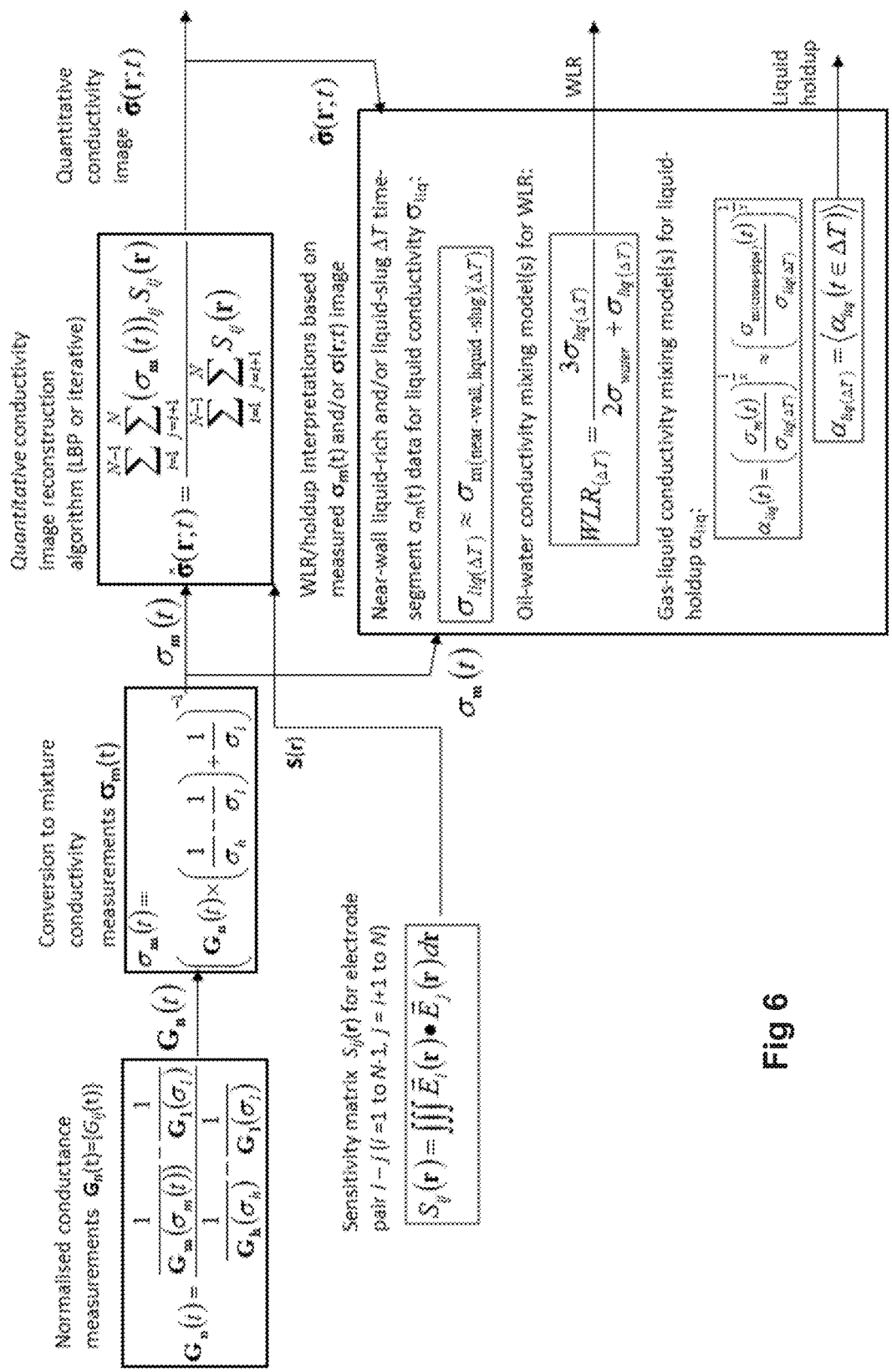
FIG. 6 diagrammatically illustrates calculation procedure for quantitative image reconstruction from ERT measurements.

A new, quantitative image reconstruction method based on the outcome of the above step is shown in FIG. 6. An LBP algorithm (as shown) and/or iterative image reconstruction algorithms use the measured multi-view $\sigma_m(t)$ as the input and give the reconstructed image of the mixture-conductivity distribution $\sigma_m(r;t)$ as output (here $r=(x,y,z)$).

Further embodiments of this disclosure use electrodes 12 to provide an electrical impedance tomography (EIT) system which is a somewhat more general approach encompassing both conductance and capacitance measurements. At an appropriate operating frequency, an EIT system can measure the conductances (G) and capacitances (C) of different electrode pairs simultaneously, for example by the use of phase-sensitive (in-phase and quadrature-phase) detection methods. The electrical admittances Y (admittance is the reciprocal of impedance) can be represented by $Y=G+j\omega C$, where $\omega$ is the angular frequency. The fluid mixture complex-conductivity can be expressed $\sigma^*_m = \sigma_m + j\omega\varepsilon_o\varepsilon_m$ (where $\varepsilon_o = 8.854$ pF/m). Alternatively, the fluid mixture complex-permittivity can be used, and is expressed $\varepsilon^*_m = \varepsilon_m + j\sigma_m/(\omega\varepsilon_o)$.

Calibration measurements may again be required. The measured raw admittances of the unknown fluid ($Y_m$), of the low complex-conductivity calibration material ($Y_l$), and of the high complex-conductivity calibration material ($Y_h$), are then as follows (from $1/Y_m = 1/Y_{contact} + 1/Y_x$):

$$\frac{1}{Y_m} = \frac{1}{Y_{contact}} + \frac{1}{Y_x(\sigma^*_m)}; \quad (202a)$$

$$\frac{1}{Y_l} = \frac{1}{Y_{contact}} + \frac{1}{Y_x(\sigma^*_l)}; \quad (202b)$$

$$\frac{1}{Y_h} = \frac{1}{Y_{contact}} + \frac{1}{Y_x(\sigma^*_h)}; \quad (202c)$$

The fluid only (unknown) admittances $Y_x$ can be assumed to be proportional to the complex-conductivity $\sigma^*_m$ of the bulk fluid as follows (where k are proportional/geometrical constants for the different electrode pairs), viz.

$$Y_x(\sigma^*_m) = G_x(\sigma_m) + j\omega\varepsilon_o C_x(\varepsilon_m) = k\sigma_m + j\omega\varepsilon_o k\varepsilon_m = k\sigma^*_m \quad (204a)$$

$$Y_x(\sigma^*_l) = G_x(\sigma_l) + j\omega\varepsilon_o C_x(\varepsilon_l) = k\sigma_l + j\omega\varepsilon_o k\varepsilon_l = k\sigma^{*l} \quad (204b)$$

$$Y_x(\sigma^*_h) = G_x(\sigma_h) + j\omega\varepsilon_o C_x(\varepsilon_h) = k\sigma_h + j\omega\varepsilon_o k\varepsilon_h = k\sigma^*_h \quad (204c)$$

The normalized admittances $Y_n$ (from the raw admittances $Y_m$) are derived similarly to the normalised capacitances (Equation 6) or normalised conductances (Equation 106), as follows:

$$Y_n = \frac{\frac{1}{Y_m} - \frac{1}{Y_l}}{\frac{1}{Y_h} - \frac{1}{Y_l}} \quad (206)$$

From Equations (202a) to (202c), and Equations (204a) to (204c), the (measured) normalised admittances $Y_n$ can then be related to the ultimately desired (fluid-only) mixture complex conductivity $\sigma^*_m$, as follows:

$$Y_n = \frac{\left(\frac{1}{Y_{contact}} + \frac{1}{Y_x(\sigma^*_m)}\right) - \left(\frac{1}{Y_{contact}} + \frac{1}{Y_x(\sigma^*_l)}\right)}{\left(\frac{1}{Y_{contact}} + \frac{1}{Y_x(\sigma^*_h)}\right) - \left(\frac{1}{Y_{contact}} + \frac{1}{Y_x(\sigma^*_l)}\right)} \quad (207)$$

$$= \frac{\frac{1}{Y_x(\sigma^*_m)} - \frac{1}{Y_x(\sigma^*_l)}}{\frac{1}{Y_x(\sigma^*_h)} - \frac{1}{Y_x(\sigma^*_l)}}$$

$$= \frac{\frac{1}{\sigma^*_m} - \frac{1}{\sigma^*_l}}{\frac{1}{\sigma^*_h} - \frac{1}{\sigma^*_l}}$$

In this way, the electrode contact/wall impedances $Z_{contact} = 1/Y_{contact}$ (and the sensors' geometrical factors k) are substantially removed in the normalised (measured) admittances $Y_n$, but the resulting normalized admittances $Y_n$ are a nonlinear function of the desired mixture-complex conductivity $\sigma^*_m$ to be measured and/or to be imaged.

In embodiments of this disclosure, the normalised admittances $Y_n$ are converted to a fundamental physics parameter which is the mixture complex-conductivity $\sigma^*_m$, and this mixture-conductivity ($\sigma^*_m$) is the input to the image reconstruction step, removing the issues of the nonlinearity in the imaging domain and of the empirical correlations/calibrations in the subsequent step(s) of determining phase fractions based on $Y_n$. Phase fractions may be determined from $\sigma^*_m$, based on complex conductivity-mixing models—or on their real and imaginary parts.

Rearranging Equation (207) gives:

$$\sigma^*_m = \frac{1}{Y_n\left(\frac{1}{\sigma^*_h} - \frac{1}{\sigma^*_l}\right) + \frac{1}{\sigma^*_l}} \quad (208)$$

Figure 7:
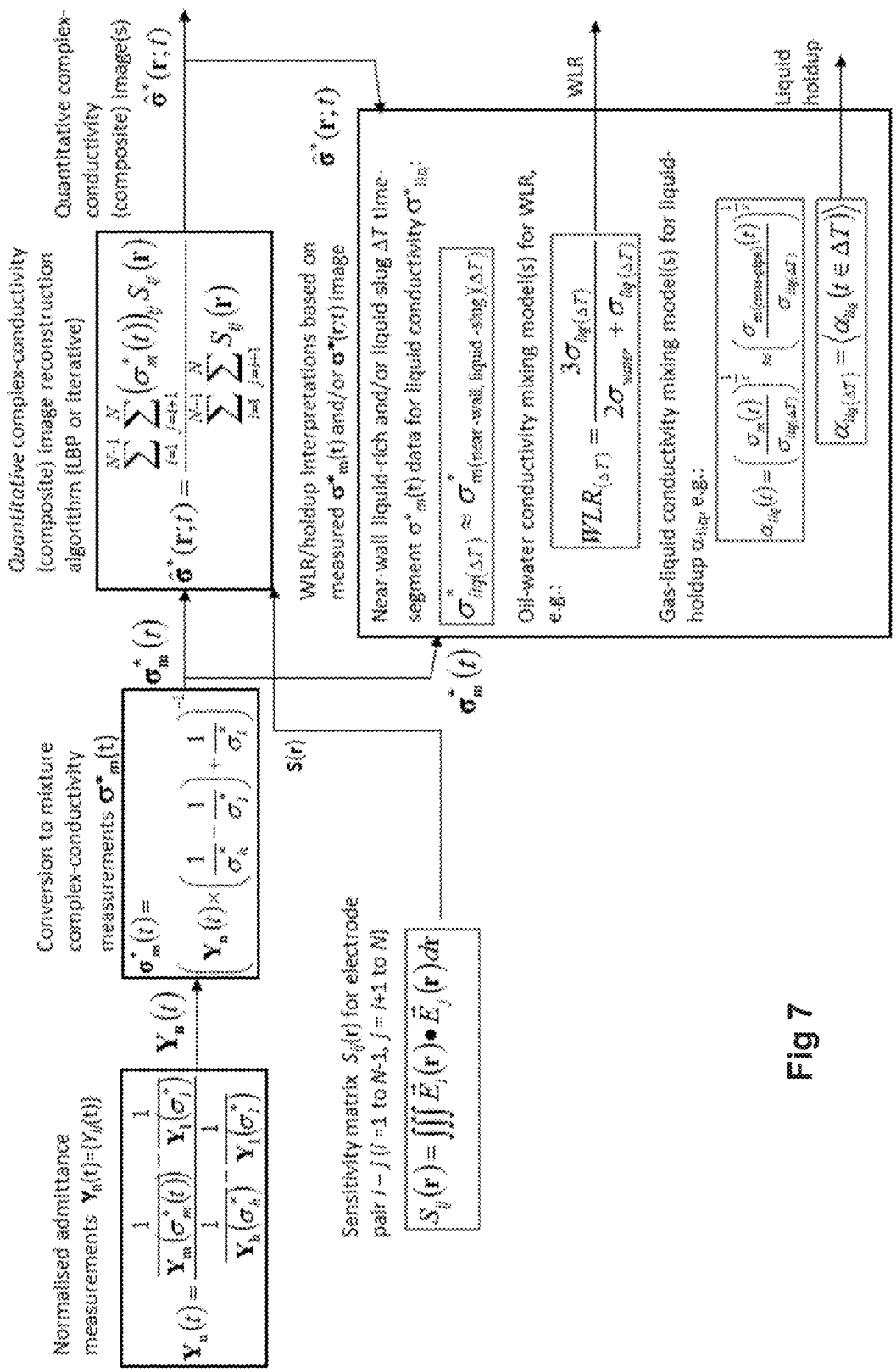
FIG. 7 diagrammatically illustrates calculation procedure for quantitative image reconstruction from EIT measurements.

A new, quantitative image reconstruction method based on the outcome of the above step is shown in FIG. 7. An LBP algorithm (as shown) and/or the corresponding iterative image reconstruction algorithms, uses the measured $\sigma^*_m$ as the input and provides a reconstructed image of the mixture-conductivity distribution $\sigma^*_m(r)$ as output.

A possibility, in yet further embodiments, is that the electrodes 12 are replaced with coils used as sensors to measure mutual-inductance between pairs of coils. The measurements of inductance may then be processed in a manner analogous to the above described processing of capacitance, conductance or impedance measurements in order to determine magnetic permeability of the multiphase flow and/or eddy-current conductivity of the flow independent of effects arising externally to the fluid flow itself. Conductivity may have general applicability; magnetic permeability may be unable to differentiate between water, oil and gas phases but may be used to observe some metallic solid particles entrained in the multiphase fluid flow.

The mixture permittivity $\varepsilon_m$ or mixture conductivity $\sigma_m$ calculated, for example, from Equation (8) or (108) respectively, or obtained from mixture complex-conductivity $\sigma^*_m$ from Equation (208), from one or more pair of sensors (electrodes and/or coils), can be used with dielectric mixing models to derive the phase fractions of the constituents of a mixture. For instance, the WLR of a well-mixed liquid-liquid mixture can be calculated by using a known mixing model relating the liquid (mixture) permittivity to the oil or water permittivity and the WLR. For water-continuous liquids, a mixing model relating the liquid (mixture) conductivity (from electrical resistance tomography ERT sensor or from the conductance component of an electrical impedance tomography EIT sensor) to the water conductivity and the WLR can be used. For example, for water-continuous homogeneous liquids, the Ramu-Rao mixing models can be used, viz:

$$\varepsilon_{liquid} = \varepsilon_{water}\frac{2wlr}{3 - wlr} \quad (9a)$$

$$\sigma_{liquid} = \sigma_{water}\frac{2wlr}{3 - wlr} \quad (9b)$$

For oil-continuous homogeneous liquids, the corresponding Ramu-Rao relations are:

$$\varepsilon_{liquid} = \varepsilon_{oil}\frac{1 + 2wlr}{1 - wlr} \quad (10a)$$

$$\sigma_{liquid} = \sigma_{oil}\frac{1 + 2wlr}{1 - wlr} \quad (10b)$$

However, Equation 10(b) may not be useful because the conductivity of an oil phase is much lower than that of formation water and is substantially close to zero. Equation (10a) also indicates that the mixture permittivity of an oil-continuous liquid is largely independent of the water permittivity and/or water conductivity.

The inverses of the Equations (9a), (9b) and (10a) are respectively as follows:

$$wlr = \frac{3\varepsilon_{liquid}}{2\varepsilon_{water} + \varepsilon_{liquid}}, \text{ water-continuous } (ERT, EIT) \quad (11a)$$

$$wlr = \frac{3\sigma_{liquid}}{2\sigma_{water} + \sigma_{liquid}}, \text{ water-continuous } (ERT, EIT) \quad (11b)$$

$$wlr = \frac{\varepsilon_{liquid} - \varepsilon_{oil}}{\varepsilon_{liquid} + 2\varepsilon_{oil}}, \text{ oil-continuous } (ECT, EIT) \quad (12a)$$

A complex-permittivity mixing model can be generally expressed as below (for a well-mixed, or a layered or other oil/water liquid mixture), $$wlr = f_{water-continuous}(\varepsilon^*_{liquid}, \varepsilon^*_{water}, \varepsilon^*_{oil}) \quad (13a)$$

$$wlr = g_{oil-continuous}(\varepsilon^*_{liquid}, \varepsilon^*_{water}, \varepsilon^*_{oil}) \quad (13b)$$

From the measured gas-liquid flow-mixture (normalized) electrical admittances Y measured at frequency $\omega$ (Y=G+ j$\omega$C) by electrical impedance tomography (EIT), or the electrical conductances Y=G from electrical resistance tomography (ERT), or the electrical capacitances Y=j$\omega$C from electrical capacitance tomography (ECT), the gas-liquid mixture complex-permittivity $\varepsilon^*_{mixture} = \varepsilon_m + \sigma_m/(j\omega\varepsilon_o)$ can be generally expressed as (the dependences on the temperature and/or pressure and on the salt species are implicit):

$$\varepsilon^*_{mixture} = \text{Func}(\varepsilon^*_{liquid}(wlr, \varepsilon^*_{water}, \varepsilon_{oil}), \varepsilon_{gas}, \alpha_{gas}; \text{flow regime}) \quad (14)$$

The "flow regime" may include gas or liquid (water- or oil-) continuous state as well as the conventional flow regimes such as plug, slug, stratified and annular flows.

For instance, for an annular gas-liquid flow, the gas fraction $\alpha_{gas}$ (over the measurement cross section of electrical tomography sensors) can be estimated from the data-processing of the measured multi-view electrical admittances $Y=G+j\omega C$ and/or from the processing of the resulting reconstructed image(s) of the gas-liquid mixture complex-permittivity $\varepsilon^*_{mixture}$ (for example, there could be two separate images consisting of a mixture permittivity $\varepsilon_m$ image and a mixture conductivity $\sigma_m$ image).

More specifically, for a vertical gas-liquid flow distribution (including the special case of oil-water flows with GVF=0% by volume), instantaneously, the flow tends to have a gas-rich core within a liquid-rich annulus over the measurement section. Time-average wise, the gas-liquid distribution also tends to be axi-symmetric. From a measure of the liquid fraction $\alpha_{liquid}$ (potentially from multi-view $\varepsilon_m$ and/or $\sigma_m$ measurements and/or from their reconstructed $\varepsilon_m$ and/or $\sigma_m$ distributions), the cross-pipe electrode-pair measurement(s) of the mixture permittivity ($\varepsilon_{mixture}$) or conductivity ($\sigma_{mixture}$) can, for example, be expressed as a function of the liquid-mixture permittivity ($\varepsilon_{liquid}$) or conductivity ($\sigma_{liquid}$) as follows:

$$\varepsilon_{mixture} \alpha_{liquid}{}^{x}(\varepsilon_{liquid}-\varepsilon_{gas})+\varepsilon_{gas} \quad (15a)$$

$$\sigma_{mixture}=\alpha_{liquid}{}^{y}(\sigma_{liquid}) \quad (15b)$$

where x and y are empirical exponents.

The inverse forms of the above relations are simply:

$$\varepsilon_{liquid} = \frac{\varepsilon_{mixture} - \varepsilon_{gas}}{(\alpha_{liquid})^{\frac{1}{x}}} + \varepsilon_{gas} \quad (16a)$$

$$\sigma_{liquid} = \frac{\sigma_{mixture}}{(\alpha_{liquid})^{\frac{1}{y}}} \quad (16b)$$

Equations (11a), (11b) or (12a) can then be used to derive the desired WLR, as illustrated as an example in FIG. 4 for ECT, in FIG. 6 for ERT, and in FIG. 7 for EIT (from the measured conductivity-component of the measured complex-conductivity).

Since electrical tomography sensors provide measurements covering different parts of the pipe cross-section, and at a high temporal resolution (typically>100 Hz), near-wall regional measurements may be used to provide an estimate of the pipe-averaged WLR by measuring the mixture permittivity and/or mixture conductivity of the liquid-rich flow near the pipe wall, and/or of the liquid-rich slug in the case of gas-liquid slug flows (with proper processing and short-time averaging of the slug-flow time-series data using tomography images as needed). (The WLR of a multiphase-flow typically changes slowly with time, and for a vertical pipe, are substantially the same over the pipe cross section). For an electrical tomography system (calibrated from a suitable normalization process such as Equation (8) for ECT and Equation (108) for ERT, this results in direct estimate(s) of the liquid-mixture permittivity $\varepsilon_{liquid} \cong \varepsilon_{mixture}$(near-wall, liquid-slug) and/or the conductivity $\sigma_{liquid} \cong \sigma_{mixture}$ (near-wall,liquid-slug), see FIG. 4 and FIG. 6, respectively. The WLR can then be estimated from Equation (11a), (11b), or (12a), given the single-phase oil or water permittivity and/or conductivity at the prevailing line temperature and pressure).

Then, by using cross-pipe mixture permittivity ($\varepsilon_{mixture(cross-pipe)}$) and/or mixture conductivity ($\sigma_{mixture}$ (cross-pipe)) measurements (with long-time averaging to capture sufficient number of gas/liquid slugs if present), which are more sensitive to the presence of gas phase in the pipe centre, and using the liquid-mixture properties estimated from the near-wall measurements as described above [$\varepsilon_{liquid} \cong \varepsilon_{mixture}$ (near-wall,liquid-slug) and/or $\sigma_{liquid} \cong \sigma_{mixture}$ (near-wall,liquid-slug)], the liquid fraction of the multi-phase-flow can then be estimated from, for example, Equations (15a) and (15b), viz.

$$\alpha_{liquid} = \left(\frac{\varepsilon_{mixture} - \varepsilon_{gas}}{\varepsilon_{liquid} - \varepsilon_{gas}}\right)^{\frac{1}{x}} \quad (17a)$$

$$\cong \left(\frac{\varepsilon_{mixture(cross-pipe)} - \varepsilon_{gas}}{\varepsilon_{mixture(near-wall,liquid\text{-slug})} - \varepsilon_{gas}}\right)^{\frac{1}{x}} ECT, EIT$$

$$\alpha_{liquid} = \left(\frac{\sigma_{mixture}}{\sigma_{liquid}}\right)^{\frac{1}{y}} \quad (17b)$$

$$\cong \left(\frac{\sigma_{mixture(cross-pipe)}}{\sigma_{mixture(near-wall,liquid\text{-slug})}}\right)^{\frac{1}{y}} ERT, EIT$$

These exemplary liquid-holdup equations are illustrated in FIG. 4 to FIG. 7.

Examples

Figure 8:
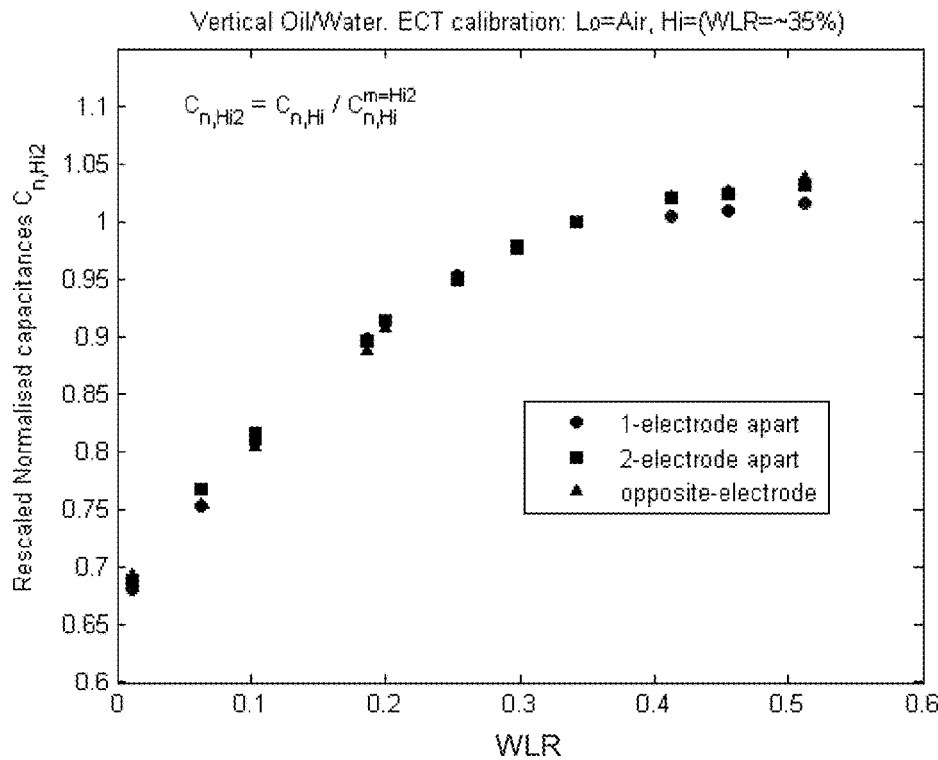
FIG. 8 graphs data for capacitance measurements on vertical oil-water flow.
Figure 9:
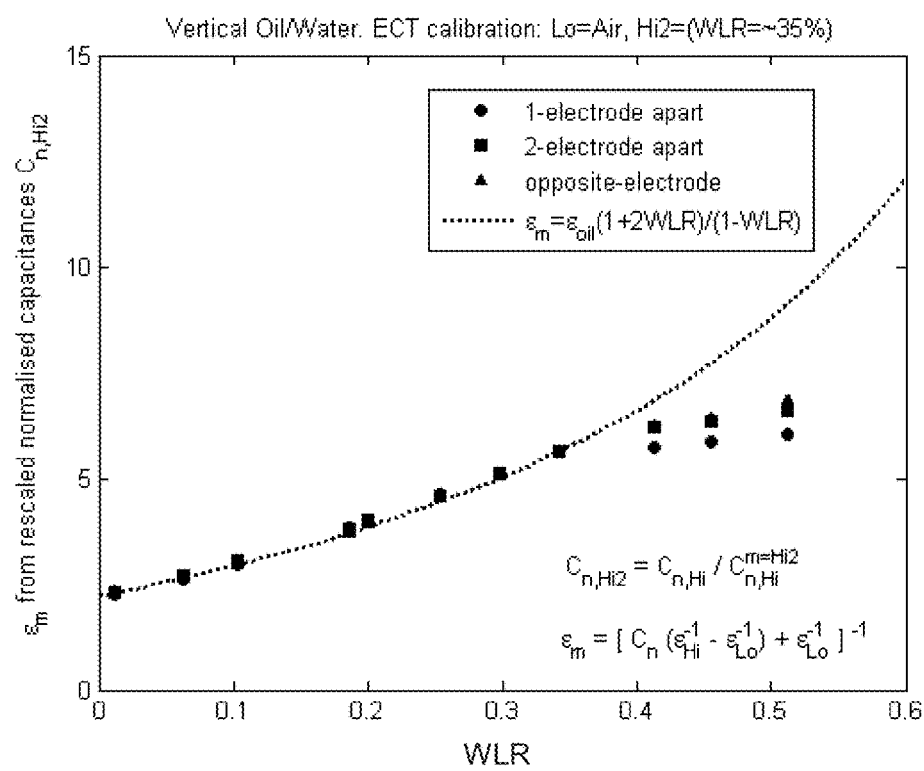
FIG. 9 graphs permittivity data computed from the capacitance data of FIG. 8.
Figure 10:
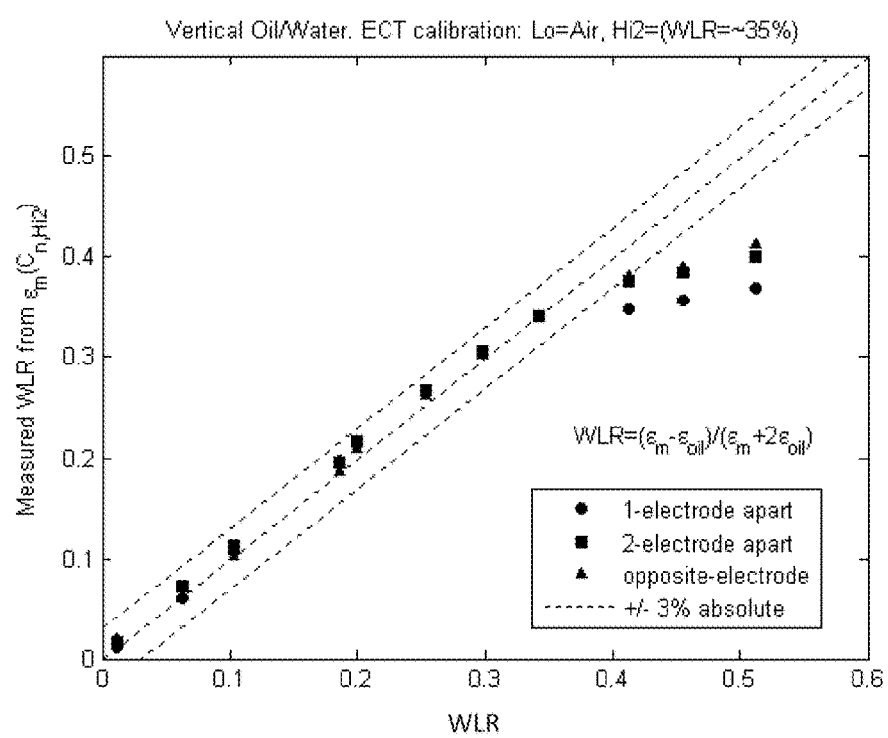
FIG. 10 graphs water-liquid ratio (WLR) computed from the data of FIG. 9.

FIGS. 8, 9 and 10 show data for electrical capacitance measurements on well-mixed vertical oil-water flows. The measurements were obtained using an arrangement as in FIG. 1 with eight electrodes arranged around a section of pipe made of the engineering plastic polyether ether ketone (PEEK). The eight electrodes were used to measure all 28 capacitances between electrode pairs. The measurements between immediately adjacent electrodes were not used because of the amount of pipe wall in the path between such electrodes. The other 20 measurements belonged to three groups, which were:

8 data points for measurements between electrodes one apart (i.e., 1-3, 2-4, etc. with one in between, as for example measurement path 21 shown chain dashed in FIG. 1), 8 data points for measurements between electrodes two apart (i.e., 1-4, 2-5, etc. with two in between, as for example measurement path 22 shown chain dashed in FIGS. 1) and 4 data points for diametrically opposite electrodes (1-5, 2-6 etc. as for example measurement path 23 shown chain dashed in FIG. 1).

The data measured by ECT sensors may be saved in the form of normalised capacitances $C_n$ (rather than the raw capacitances $C_m$) based on using empty-pipe data as the $C_l(\varepsilon_l)$ (its rescaling is described more fully in Explanatory Comment 1, below), and the full-pipe oil-water mixture data as the $C_h(\varepsilon_h)$, with WLR=~35% (its rescaling is described more fully in Explanatory Comment 2, below).

FIG. 8 shows measured (series-model) normalized capacitances $C_n$ from Equation (6) above rescaled based on the equation as indicated. The data points shown are spatial-averaged for the 8 or 4 measurements in each group and time-averaged over 60 s. From this data it can be seen that the measured normalized capacitances $C_n$ for full-pipe oil (WLR=~0, GVF=0) are approx. 0.65 ($C_n$=0 for empty-pipe), and increase almost linearly with increasing WLR up to WLR approx. 0.35. The jump in the value of $C_n$ from 0 to ~0.65 for a small change in the permittivity ($\varepsilon$=1 to 2.2) is very large. The apparent nonlinearity in $C_n$ against WLR for WLR over 0.35 was attributed to limitation in the ECT sensors or the electronics linear dynamic range; the nonlinearity effect of the pipe-wall capacitance is substantially removed in the measured normalized capacitances $C_n$ (Equation (7) above).

FIG. 9 shows the corresponding values of oil-water mixture permittivity $\varepsilon_m$ derived using Equation (8) above with $\varepsilon_l=1.0$, $\varepsilon_h=5.62$ (using flow data with reference WLR=0.3415). There was excellent agreement with the Ramu-Rao mixing-model predictions (for homogeneous liquid-liquid mixture, Equation (10a) above. The expected $\varepsilon_{oil}$ of approx. 2.2 (at WLR~0) was obtained from FIG. 7 by the use of Equation (8) above with the ECT sensors calibrated at the gas-point and the oil-water mixture point (at WLR approx. 35%).

FIG. 10 shows the WLR derived using the Ramu-Rao liquid-liquid mixing-model (Equation (12a) above).

Explanatory Comment 1. The normalized capacitances can be rescaled from those ($C_{n,L=air}$) using empty-pipe air as the low-calibration to those ($C_{n,L=oil}$) using full-pipe oil. Starting from Equation (6) above, it is possible to derive $C_{n,L=oil}=(1+C_c)C_{n,L=air}-C_c$ from the following manipulations:

$$C_{n,L=air} = \frac{1/C_m - 1/C_{air}}{1/C_h - 1/C_{air}}$$

$$= \frac{(1/C_m - 1/C_{oil}) + (1/C_{oil} - 1/C_{air})}{(1/C_h - 1/C_{oil}) + (1/C_{oil} - 1/C_{air})}$$

$$= \frac{\left(\frac{1/C_m - 1/C_{oil}}{1/C_h - 1/C_{oil}}\right) + \left(\frac{1/C_{oil} - 1/C_{air}}{1/C_h - 1/C_{oil}}\right)}{1 + \left(\frac{1/C_{oil} - 1/C_{air}}{1/C_h - 1/C_{oil}}\right)}$$

$$= \frac{C_{n,L=oil} + C_c}{1 + C_c}$$

where $$C_c = \left(\frac{1/C_{oil} - 1/C_{air}}{1/C_h - 1/C_{oil}}\right) = \frac{C_{n,L=air}^{m=oil}}{1 - C_{n,L=air}^{m=oil}}$$

$$C_{n,L=air}^{m=oil} = \frac{1/C_{oil} - 1/C_{air}}{1/C_h - 1/C_{air}},$$

Explanatory Comment 2. It may be necessary in the post-processing to rescale the (saved) normalized capacitances with a different high-calibration, from those ($C_{n,H=h1}$) using full-pipe oil-water with e.g. WLR=50% (where there is a marked nonlinear response) to those ($C_{n,H=h2}$) using full-pipe oil-water with a lower WLR, e.g. WLR=~35%. Starting from Equation (6) above, it is possible to derive that $$C_{n,H=h2} = C_{n,H=h1}/C_{n,h=h1}^{m=h2}$$

from the following algebraic manipulations:

$$C_{n,H=h1} = \frac{1/C_m - 1/C_l}{1/C_{h1} - 1/C_l}$$

$$= \frac{1/C_m - 1/C_l}{(1/C_{h2} - 1/C_l) + (1/C_{h1} - 1/C_{h2})}$$

$$= \frac{\left(\frac{1/C_m - 1/C_l}{1/C_{h2} - 1/C_l}\right)}{1 + \frac{1/C_{h1} - 1/C_{h2}}{1/C_{h2} - 1/C_l}}$$

$$= \frac{C_{n,H=h2}}{\left(\frac{1/C_{h1} - 1/C_l}{1/C_{h2} - 1/C_l}\right)}$$

$$= C_{n,H=h1}^{m=h2} C_{n,H=h2}$$

Because of the axial-symmetry and homogeneity of the well-mixed oil-water flow, FIG. 9 shows little difference in the ECT derived mixture permittivity ($\varepsilon_m$) with WLR up to approx. 35%, among the '1-electrode-apart' (near-wall) measurements, near cross-pipe ('2-electrode-apart') and cross-pipe ('opposite-electrode') measurements. The ECT derived WLR from the $\varepsilon_m$ data (FIG. 10) is within approx. ±2% absolute, for WLR <approx. 35% by using the inverse Ramu-Rao mixing-model at Equation (12a) above.

Figure 11:
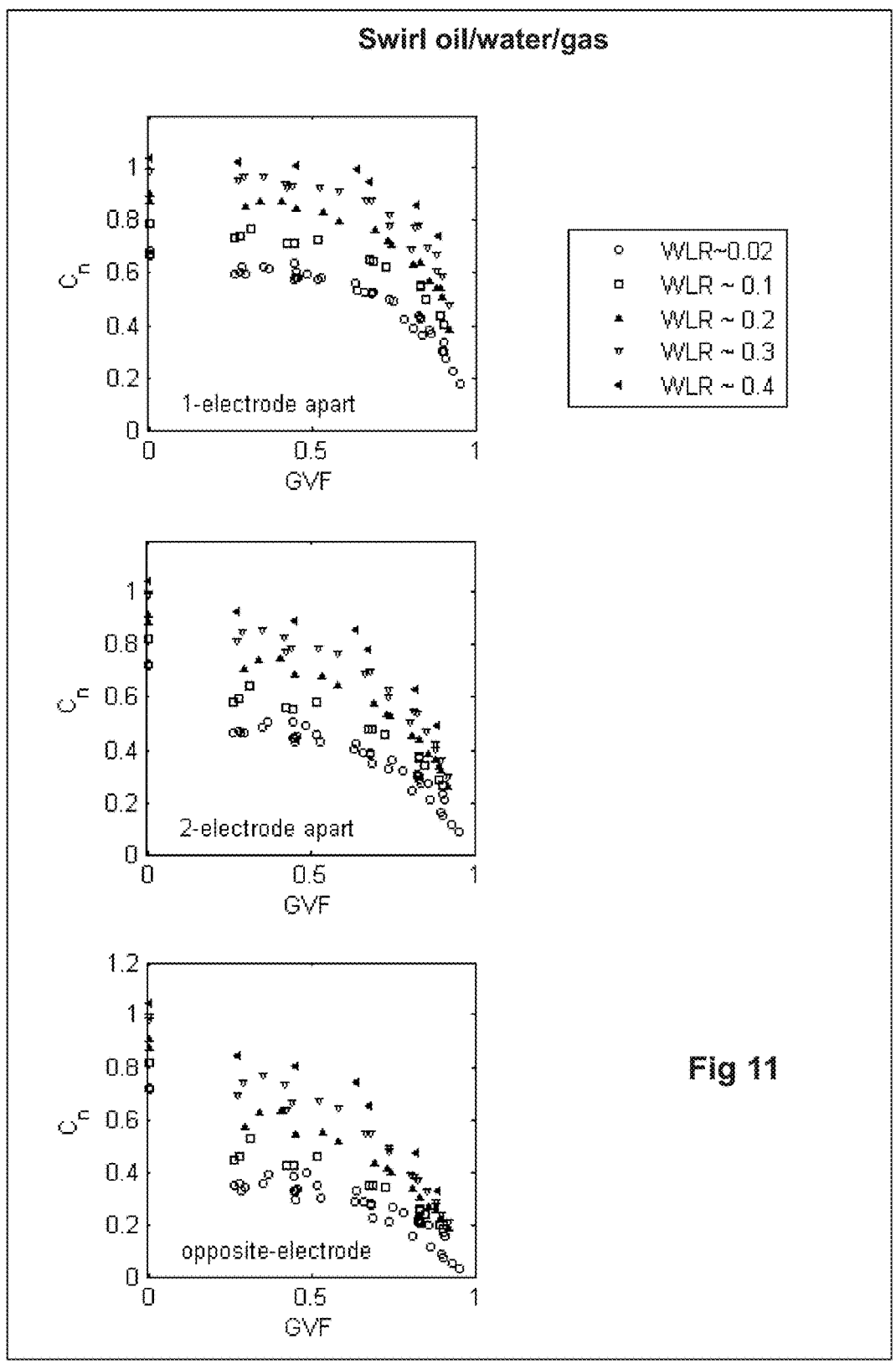
FIGS. 11 and 12 show graphs similar to those in FIGS. 8 and 9 for a conditioned oil-water-gas annular-type flow.
Figure 12:
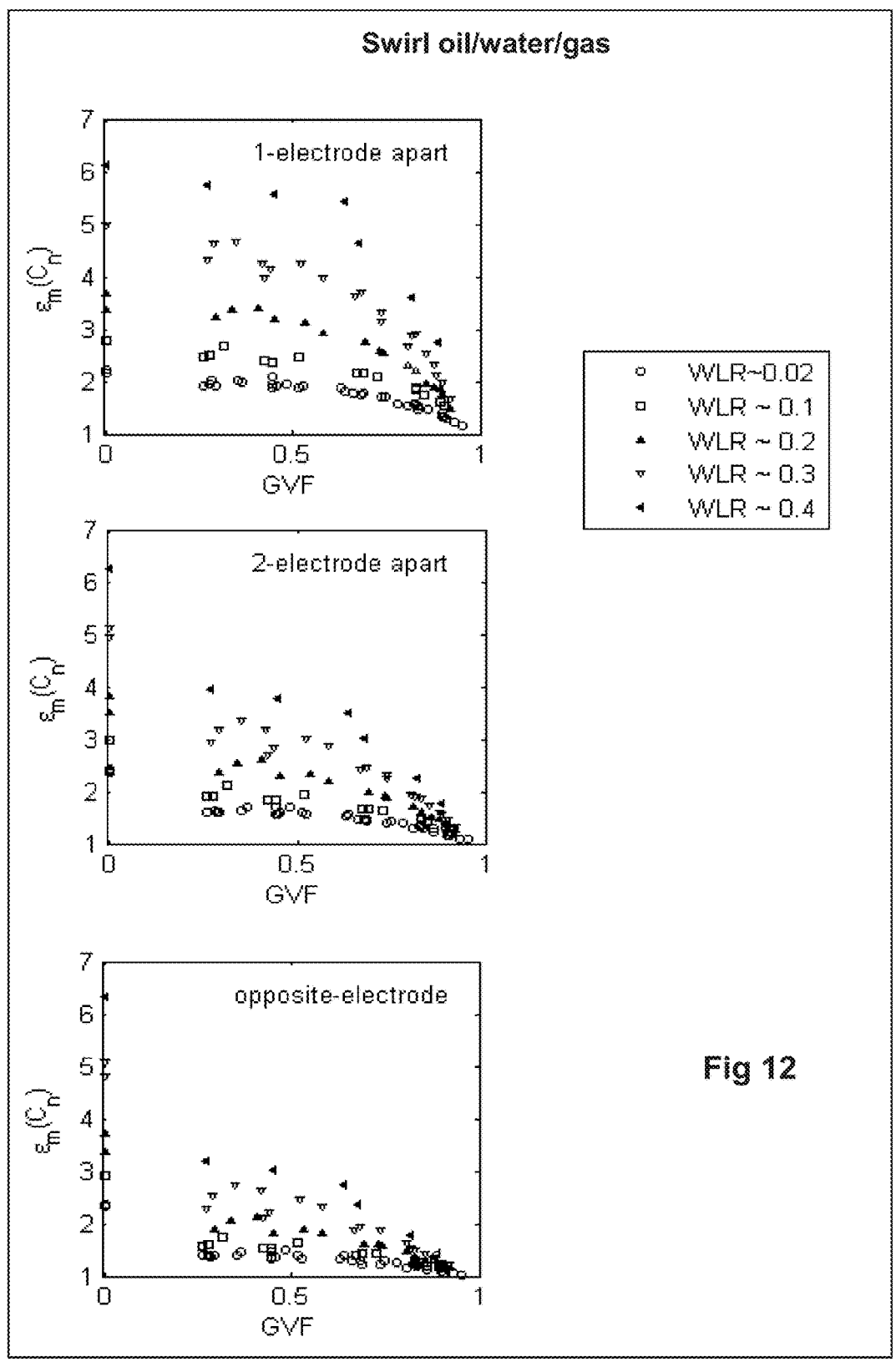

FIGS. 11 and 12 show data measured in the same way as for FIGS. 8 and 9 for flows of gas and liquid with various WLR's. The gas-liquid flows were conditioned by swirling so that the gas formed a core at the centre of the flow and was surrounded by the liquid annulus flow. FIG. 11 contains three separate plots showing the normalised capacitances $C_n$ measured by different electrode-pair groups at different water-liquid ratios. From these measurements the corresponding gas-liquid mixture permittivity $\varepsilon_m$ was derived by the use of Equation (8) above and is shown in the corresponding graphs in FIG. 12.

As a check on accuracy, the near-wall and liquid-slug permittivities obtained from electrodes one apart were used to calculate WLR's. Up to a gas volume fraction of 90%, these calculated values were accurate to ±5% absolute.

Figure 13:
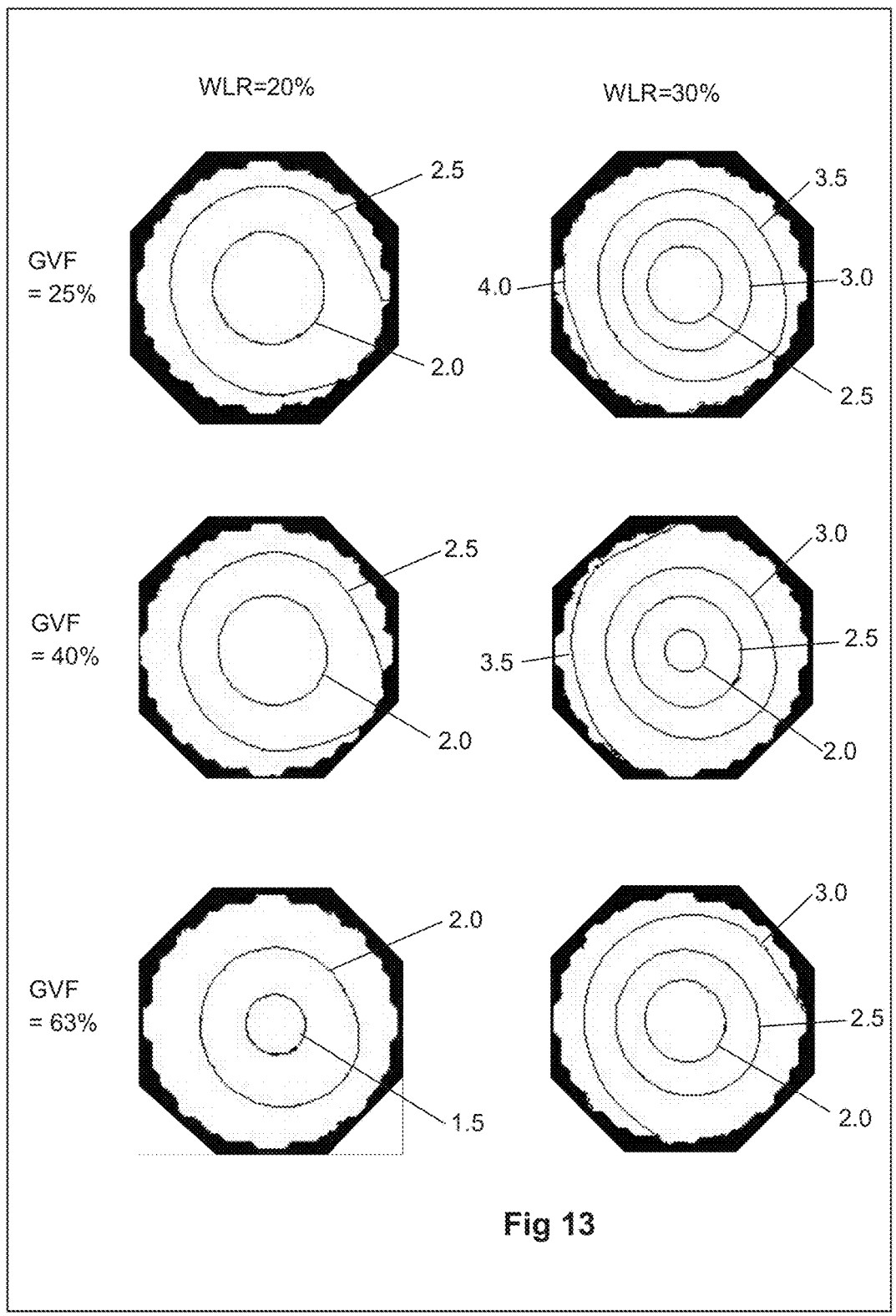
FIG. 13 shows reconstructed spatial distributions of permittivity.

Quantitative images of mixture-permittivity spatial distributions for the gas-liquid swirl flows were reconstructed using multi-view permittivity values $\varepsilon_m$ as input as in FIG. 4. Images averaged over 60 seconds are shown in FIG. 13, with WLR=~20% in the left column and WLR=~30% in the right column. There are images for each WLR with GVF=~25%, ~40% and ~63%. These images were composed of pixels, with a computed permittivity value associated with each pixel. The images could be displayed on screen or printed and if desired these permittivity values could be represented by colouring.

All the images in FIG. 13 show permittivity increasing from the centre of the pipe (where there is the gas-rich core) towards the periphery where there is liquid-rich annulus. In FIG. 13 curved lines (analogous to contour lines on a map) connect points with equal permittivity values. Taking the top left image in FIG. 13 as an example, it can be seen that a central region with permittivity below 2.0 was surrounded by a region with permittivity between 2.0 and 2.5 and this was partially surrounded by a region of permittivity above 2.5. At the bottom left, the image for a GVF of 63% and the same WLR of 20% had region with permittivity below 1.5 at the centre. With the higher WLR of approx. 30%, at the right of FIG. 13, it can be seen that permittivities were generally higher.

Figure 14:
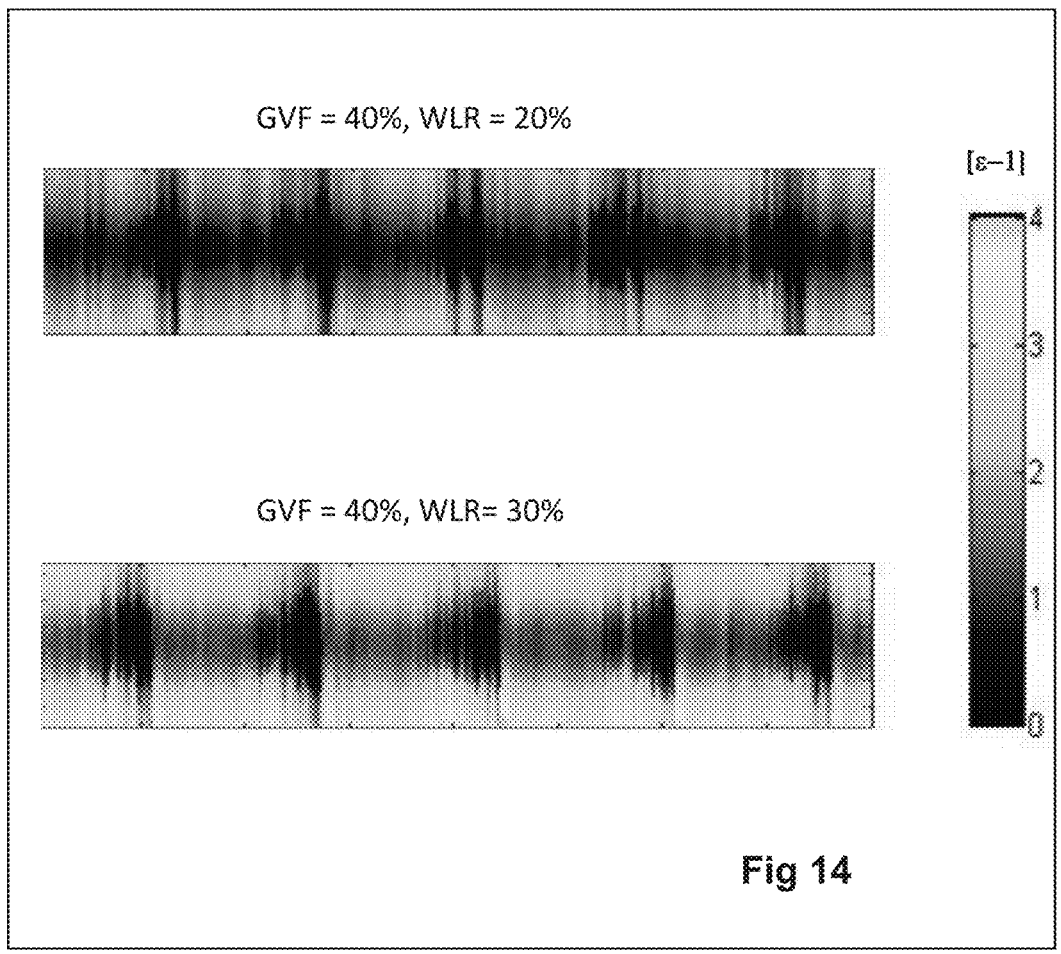
FIG. 14 shows reconstructed temporal distributions of permittivity for some of the conditioned oil-water-gas annular-type flows.

Quantitative images of mixture-permittivity temporal distributions were also reconstructed and are shown in FIG. 14 for two combinations of WLR and GVF. The reconstruction used gas-liquid mixture-permittivity data (output of the Equation (8)) as input to the linear back-projection (LBP) algorithm shown in FIG. 4. In each diagram, the horizontal axis is representative of time. Images with an imaging frame rate of approx. 100 frames per second were reconstructed and displayed (corresponding to a time interval of 8 seconds), representing permittivities across a diameter as a grey scale, and then these images are displayed as a sequence extending along the time axis. The increase in the actual permittivity (with a brighter grey-scale level) for the outer liquid layer, due to the increase in the multiphase-flow liquid WLR (20% to 30%), is clearly captured by the use of the new quantitative image reconstruction algorithm.

It is further possible to convert mixture complex-permittivity/-conductivity spatial and temporal images to images of gas, oil and water holdups, and/or of WLR, by the use of permittivity and/or conductivity mixing models.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:

1. A tomography system for determining properties of flowing multiphase fluid, comprising:
   a duct having a duct wall and interior space within the duct wall for carrying a flow of a multiphase fluid;
   a plurality of sensors at positions distributed substantially evenly around the duct wall on a planar cross section through the duct transverse to the duct axis, for making a plurality of measurements of electrical or magnetic properties through the multiphase fluid, wherein the sensors are electrodes that measure data values representative of capacitance, resistance, conductance or admittance between a plurality of pairs of electrodes in the plane of the cross section or the sensors are coils that measure data values representative of inductance between a plurality of pairs of coils in the plane of the cross section; and
   a processor receiving the measured data values from the sensors and configured to compute from the measured data values to derive computed quantitative values of at least one property selected from permittivity, conductivity, magnetic permeability and complex-conductivity of the multiphase fluid within the duct, which are independent of effects external to the fluid flow.

2. The system of claim 1, wherein deriving the computed quantitative values selected from permittivity, conductivity, permeability and complex-conductivity of the multiphase fluid from the measured data values comprises determining normalized values representative of at least one of capacitance, resistance, conductance, inductance and admittance exclusively of the multiphase fluid within the duct, and converting the normalized capacitance, resistance, conductance, or admittance to the quantitative values of permittivity, conductivity, permeability or complex-conductivity of the multiphase fluid within the duct.

3. The system of claim 1, which is an electrical tomographic system wherein the sensors are electrodes that measure values representative of capacitance, resistance, conductance or admittance between the plurality of pairs of electrodes at positions distributed around the exterior of the duct wall and the processor receiving measurement data from the electrodes is configured to determine a plurality of quantitative values of permittivity, conductivity or complex-conductivity of the multiphase fluid within the duct.

4. The system of claim 1, wherein the sensors are coils that measure values representative of inductance between the plurality of pairs of coils at positions distributed around the exterior of the duct wall and the processor receiving measurement data from the coils is configured to determine a plurality of quantitative values of conductivity or magnetic permeability of the multiphase fluid within the duct.

5. The system of claim 1, wherein the processor is configured to compute at least one of a water-in-liquid-ratio and a liquid fraction of the multiphase fluid from one or more of the plurality of quantitative values of permittivity, conductivity or complex-conductivity.

6. The system of claim 1, wherein the processor is configured to compute at least one image showing spatial distribution of permittivity, conductivity, magnetic permeability or complex-conductivity of the multiphase fluid within the planar cross-section of the duct.

7. The system of claim 1, wherein the processor is configured to compute at least one image showing temporal distribution of permittivity, conductivity, magnetic permeability or complex-conductivity of the multiphase fluid within the planar cross-section of the duct.

8. A computer implemented method of measuring properties of a multiphase fluid flowing within a duct, comprising:
   making a plurality of measurements representative of capacitance, resistance, conductance, inductance or admittance between a plurality of pairs of sensors distributed substantially evenly around a planar cross section through the fluid transverse to the direction of flow within the duct; and
   computing permittivity, conductivity, magnetic permeability or complex-conductivity of the multiphase fluid from the measurements made;
   wherein the computed permittivity, conductivity, magnetic permeability or complex-conductivity is exclusively that of the multiphase fluid independent of effects external to the flow of the multiphase fluid.

9. The method of claim 8, wherein measurements are between sensors that are electrodes or coils mounted around the duct carrying the flowing multiphase fluid and the method further comprises:
   determining normalized values representative of capacitance, resistance, conductance, inductance or admittance at the planar cross section through the fluid, wherein the normalized values relate exclusively to the multiphase fluid and are independent of effects external to the flow of the multiphase fluid; and
   computing permittivity, conductivity, magnetic permeability or complex-conductivity of the multiphase fluid from one of the normalized values.

10. The method of claim 8, wherein measurements are between electrodes mounted outside the duct carrying the flowing multiphase fluid, and the method further comprises:
   determining normalized values representative of capacitance, resistance, conductance, inductance or admittance at the planar cross section through the fluid, wherein the normalized values relate exclusively to the multiphase fluid and are independent of effects external to the flow of the multiphase fluid, and computing permittivity, conductivity, magnetic permeability or complex-conductivity of the multiphase fluid within the duct from one of the normalized values.

11. The method of claim 8, further comprising:
   computing at least one of a water-in-liquid-ratio and a liquid fraction of the multiphase fluid from the computed permittivity, conductivity, magnetic permeability or complex-conductivity of the multiphase fluid.

12. The method of claim 8, further comprising:
   computing one or more images showing spatial distribution of permittivity, conductivity, magnetic permeability or complex-conductivity within the cross-section through the multiphase flow.

13. The method of claim 8, further comprising:
   computing one or more images showing temporal distribution of permittivity, conductivity, magnetic permeability or complex-conductivity within the cross-section through the multiphase flow.

14. The method of claim 8, further comprising:
making a plurality of measurements representative of capacitance, resistance, conductance, inductance or admittance at one or more further cross sections through the fluid transverse to the direction of flow within the duct.

15. The method of claim 8, wherein the plurality of sensors comprises eight sensors distributed substantially evenly around the duct wall and the system is configured for making measurements representative of capacitance, resistance, conductance, inductance or admittance between all pairs of the eight sensors other than those which are adjacent to each other.

16. The method of claim 9, further comprising:
making calibration measurements representative of capacitance, resistance, inductance or admittance between pairs of sensors at the planar cross section when the duct contains single phase fluids.

17. The system of claim 1, wherein the plurality of sensors comprises eight sensors distributed substantially evenly around the duct wall and the system is configured for making measurements representative of capacitance, resistance, conductance, inductance or admittance between all pairs of the eight sensors other than those which are adjacent to each other.

18. A tomography system for determining properties of flowing multiphase fluid, comprising:
a duct having a duct wall and interior space within the duct wall for carrying a flow of a multiphase fluid;
a plurality of sensors at positions distributed substantially evenly around the duct wall on a planar cross section through the duct transverse to the duct axis, for making a plurality of measurements of electrical or magnetic properties through the multiphase fluid, wherein the sensors are electrodes that measure data values representative of capacitance, resistance, conductance or admittance between a plurality of pairs of electrodes in the plane of the cross section or the sensors are coils that measure data values representative of inductance between a plurality of pairs of coils in the plane of the cross section; and
a processor receiving the measured data values from the sensors and configured to compute from the measured data values to derive normalized values representative of the capacitance, resistance, conductance, inductance or admittance exclusively of the multiphase fluid within the duct, and to convert the normalized values of capacitance, conductance, or admittance to computed quantitative values of at least one property selected from permittivity, conductivity, magnetic permeability and complex-conductivity of the multiphase fluid within the duct, which are independent of effects external to the fluid flow.

19. A computer implemented method of measuring properties of a multiphase fluid flowing within a duct, comprising:
making a plurality of measurements representative of capacitance, resistance, inductance or admittance between a plurality of pairs of sensors at positions distributed substantially evenly around a wall of the duct and at a planar cross section through the fluid transverse to the direction of flow within the duct;
determining normalized values representative of capacitance, resistance, inductance or admittance at the one or more cross sections through the fluid, where the normalized values relate exclusively to the multiphase fluid and are independent of effects external to the flow of the multiphase fluid; and
computing permittivity, conductivity, magnetic permeability or complex-conductivity of the multiphase fluid from the normalized values representative of capacitance, resistance, inductance or admittance, wherein the computed permittivity, conductivity, magnetic permeability or complex-conductivity is exclusively that of the multiphase fluid independent of effects external to the flow of the multiphase fluid.

20. The method of claim 19, further comprising:
making calibration measurements representative of capacitance, resistance, conductance, inductance or admittance between pairs of sensors at the planar cross section when the duct contains single phase fluids.

* * * * *